US008025852B2

(12) United States Patent
Zarate

(10) Patent No.: US 8,025,852 B2
(45) Date of Patent: Sep. 27, 2011

(54) LIFTING AND PRESERVING BLOODY IMPRESSIONS FOR LAW ENFORCEMENT

(76) Inventor: Jessica Lynn Zarate, Redford, MI (US)

( * ) Notice: Subject to any disclaimer, the term of this patent is extended or adjusted under 35 U.S.C. 154(b) by 0 days.

(21) Appl. No.: 12/698,727

(22) Filed: Feb. 2, 2010

(65) Prior Publication Data

US 2010/0136208 A1 Jun. 3, 2010

Related U.S. Application Data

(63) Continuation-in-part of application No. 12/581,557, filed on Oct. 19, 2009, which is a continuation-in-part of application No. 11/952,672, filed on Dec. 7, 2007.

(60) Provisional application No. 60/873,470, filed on Dec. 7, 2006.

(51) Int. Cl.
*A61B 5/117* (2006.01)

(52) U.S. Cl. ............................ 422/430; 436/176; 427/1

(58) Field of Classification Search .................... 422/99, 422/430; 436/176; 427/1
See application file for complete search history.

(56) References Cited

U.S. PATENT DOCUMENTS

| | | | | |
|---|---|---|---|---|
| 2,986,831 | A * | 6/1961 | Terek et al. | 264/299 |
| 3,944,701 | A * | 3/1976 | Dennis et al. | 430/273.1 |
| 4,176,205 | A * | 11/1979 | Molina | 427/1 |
| 5,079,029 | A * | 1/1992 | Saunders | 427/1 |

OTHER PUBLICATIONS

I.D. Technologies, Inc., Product Catalog of Print Lifters, Nov. 28, 2006.*

* cited by examiner

*Primary Examiner* — Jill Warden
*Assistant Examiner* — Monique T. Cole
(74) *Attorney, Agent, or Firm* — Honigman Miller Schwartz and Cohn LLP

(57) ABSTRACT

A fluorogenic lifting strip containing titanium dioxide has been successful in the lifting and enhancement of impressions and bloody impressions from nonporous, semi porous and porous surfaces. The lifting strip is best when activated with an alcohol such as ethanol or methanol. When the lifting strip has dried after application it can easily be removed from the surface lifting the impression onto a contrasting white background. The lifting trip can be subsequently visualized with an ALS or Laser to fluoresce the lifted impression with optimal contrast for visualization and examination. This method is safe, easy, and effective on several surfaces of contrasting colors.

19 Claims, 2 Drawing Sheets

LIFTING AND PRESERVING BLOODY IMPRESSIONS FOR LAW ENFORCEMENT

CROSS-REFERENCE TO RELATED APPLICATION

This is a continuation-in-part application that claims priority to U.S. continuation-in-part patent application Ser. No. 12/581,557; filed Oct. 19, 2009; U.S. patent application Ser. No. 11/952,672, filed Dec. 7, 2007; and to U.S. Provisional Patent Application Ser. No. 60/873,470, filed Dec. 7, 2006, all of which are hereby incorporated by reference.

TECHNICAL FIELD

The subject invention relates to a method and apparatus for lifting bloody and other impressions from surfaces at a crime scene.

BACKGROUND OF THE INVENTION

Various impressions are frequently encountered at crime scenes and are of great importance to law enforcement officials. Impressions can include fingerprints, bloody fingerprints, hand prints, palm prints, foot prints, footwear prints, etc. Other than blood, proteinaceous impressions can include sebaceous, eccrine, saliva, semen, and vaginal secretions. Therefore, developing impressions and bloody proteinaceous impressions on various surfaces is of great interest to the forensic science community. Every finger and palm print, for example, has a series of elevated patterns known as friction ridges which are unique to each individual in the population. As a result, if friction ridges can be visualized in blood, they can be used for identification purposes.

When bloody impressions are located on light-colored surfaces they may be photographed directly, which may provide some visualization of the ridge structure. But when bloody impressions are located on dark colored surfaces there is usually not enough contrast between the bloody impression and the surface to visualize any ridge structure in the impression. Currently, there are a variety of techniques for enhancing bloody impressions on some non-porous, semi-porous and porous surfaces of varying contrasts, yet they are limited in their effectiveness (Caldwell and Kim 2002; Forsythe-Erman 2001; McCarthy and Grieve 1988; Sears and Prizeman 2000; Sears and others 2001; Sears and others 2005; Yapping and Yue 2004). These processes require using chemical reagents and are normally conducted in a laboratory setting, which may be both inconvenient and time consuming. Furthermore, immovable or bulky objects from crime scenes cannot be brought back to the laboratory for analysis. Many potentially identifiable impressions may only be photographed and not enhanced due to limitations of this nature; and this is not in the best interest of society.

Accordingly, the inventor has seen a need for technology that permits law enforcement officials to lift a bloody impression from a crime-scene surface, and to preserve it for further analysis and use. The inventor has also discovered that certain embodiments of the invention are also useful for lifting, preserving, and analyzing prints such as latent fingerprints because these embodiments produce an impression that has fluorescent characteristics when analyzed under certain light sources.

SUMMARY OF THE INVENTION

According to one aspect of the invention, there is a method of lifting bloody and other impressions from a surface including the steps of: providing a backing sheet having titanium dioxide disposed thereon; applying a liquid to the sheet to wet the titanium dioxide; applying the wetted sheet to the impression; and lifting the backing sheet to remove at least an identifiable portion of the impression from the surface. The impression so lifted will have fluorescent properties when viewed with a predetermined type of lighting such as ALS.

According to a similar aspect, there is a method of making a lifting sheet for lifting bloody and other impressions including the steps of: obtaining a porous polymeric backing sheet; preparing a coating material including titanium dioxide and at least one of the following: an acid, a surfactant, and a polymer; dispersing the titanium dioxide uniformly throughout the coating material; coating at least one side of the backing sheet with the coating material; and drying the coating material to fix it on the backing sheet.

According to another aspect of the invention, there is a strip assembly for lifting and preserving bloody impressions including: a lifting strip having a polymeric support layer and an impression contact layer carried by the support layer, where the impression contact layer includes titanium dioxide disposed uniformly over the polymeric support layer.

According to yet another aspect, there is a lifting strip assembly for lifting and preserving bloody impressions including a lifting strip including a backing layer and an impression bonding layer carried on the backing layer, the bonding layer including a material adapted to bond with the proteinaceous material in bloody impressions and preserve the impression intact; and a transparent protective layer hingedly attached to the lifting strip whereby the protective layer can be disposed over the bonding layer to cover and protect the impression after it has been lifted.

Other desirable embodiments will occur to those skilled in the art.

FIGURES IN THE DRAWINGS

The present invention will now be described, by way of example, with reference to the accompanying drawings, in which.

DESCRIPTION OF THE PREFERRED EMBODIMENTS

Figure 1:
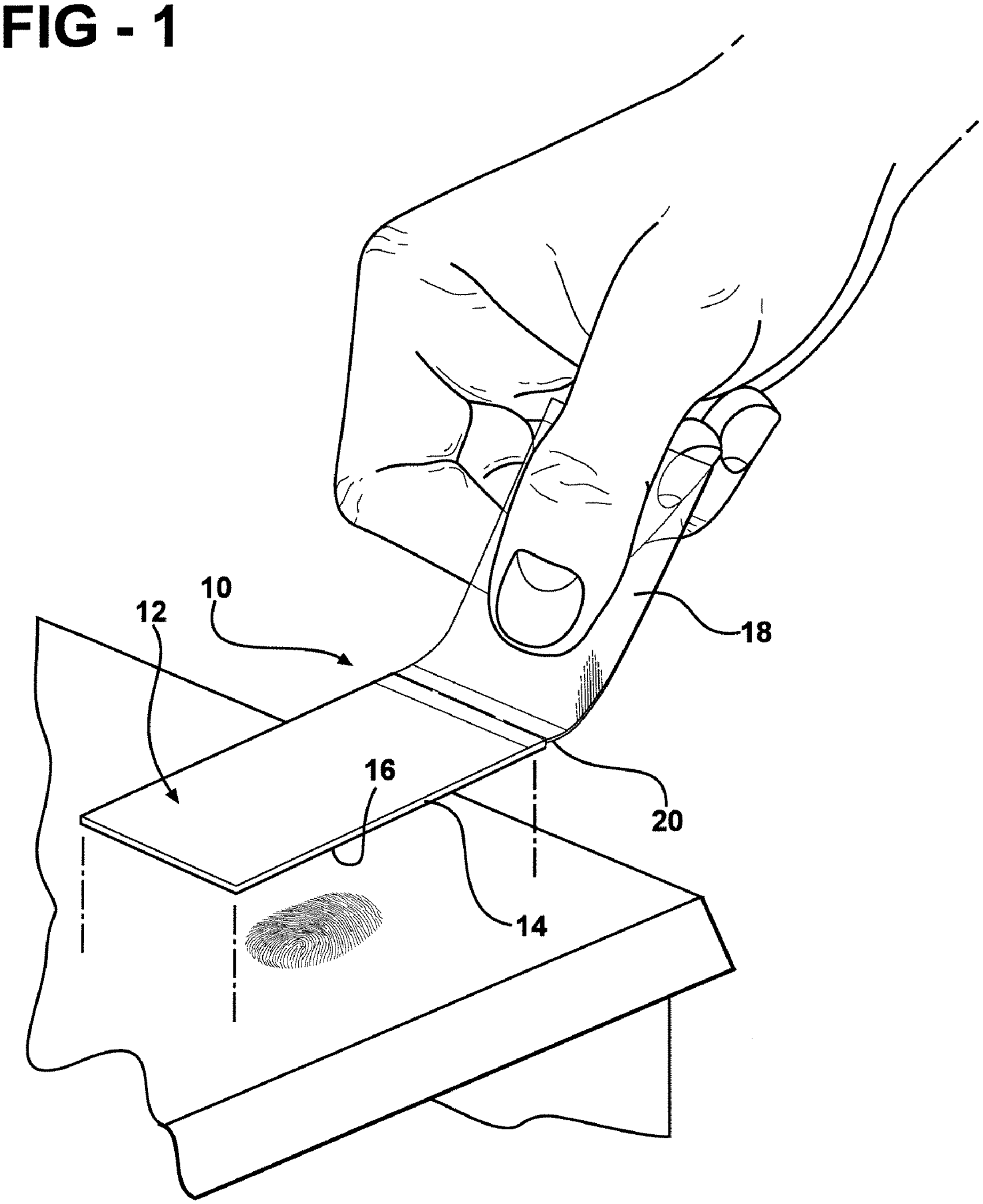
FIG. 1 is a bottom perspective view showing an embodiment of the invention being used to lift a bloody fingerprint.
Figure 2:
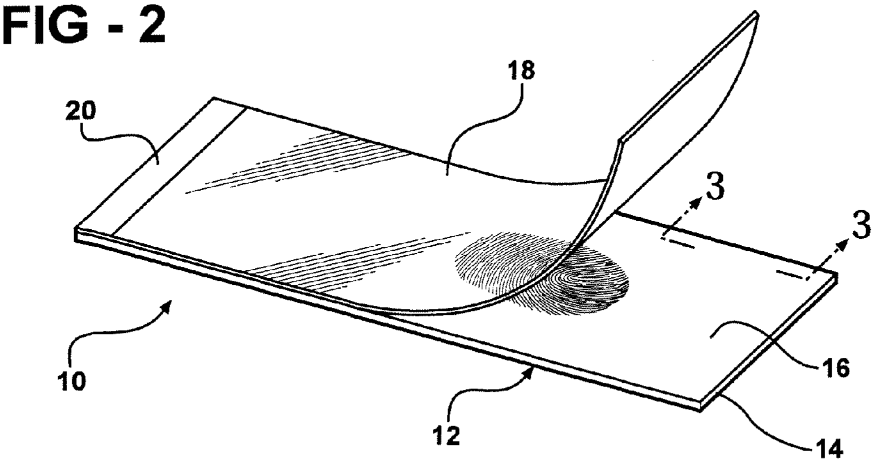
FIG. 2 is a top perspective view showing an embodiment of the invention with a fingerprint already lifted.

The present invention will now be described, by way of example, with reference to the accompanying figures in which the lifting strip assembly is generally shown at 10.

The inventor performed several studies to determine the effectiveness of a lifting strip containing titanium dioxide for lifting and enhancing bloody fingerprints from a variety of different surfaces when activated with water, methanol, or Kodak Photo-Flo 200™. As described by the relevant Material Safety Data Sheet, titanium dioxide is a non-toxic, nonflammable, fine white powder that is often used as a pigment in paints (MSDS 2006). Due to its non toxic nature, titanium dioxide is ideal reagent for the enhancement and development of bloody and latent fingerprints. Titanium dioxide has shown its effectiveness in other studies in forensic science, where it had been used successfully to enhance bloody fingerprints on dark nonporous surfaces and latent fingerprints on adhesive surfaces (Bergeron 2003; Martin 1999; Schiemer and others 2005; Wade 2002; Williams and Elliott 2005).

The blood used in this study was obtained from a healthy volunteer donor. The samples of blood were taken intravenously and drawn directly into vacutainers containing anti-coagulants by a registered nurse in a medical facility. The blood was refrigerated prior to being used and between uses. Before fingerprint depositions were made using the blood it was waned to room temperature and shaken vigorously to mix up the contents.

Fingerprints were placed on non-porous, semi-porous and porous surfaces to test the effectiveness of the lifting strip containing titanium dioxide and to determine the quality of the lifted print. The bloody fingerprints were deposited on the various surfaces using the right thumb of the analyst, which had been lightly coated with blood and pressed against the surfaces for a period of ten seconds. The seven surfaces were selected based on their surface type and the fact that they may all be found at a crime scene. The surface items were cut into 2"×2" squares prior to deposition of the bloody fingerprints. After the bloody fingerprints were deposited on the surface they were left for one hour before the print was lifted using the lifting strip.

Biore® pore strips were used in this study due to their composition, which contains titanium dioxide and their ability to adhere to bloody fingerprints when activated with water, methanol, or Kodak Photo-Flo 200™ Existing Biore® Deep Cleaning Pore Strips are covered by one or more of the U.S. Pat. Nos. 5,512,277, 6,299,605, 6,306,382, 6,042,844, 6,221,382 and D 388,534. The teachings of these patents are incorporated herein by reference. Obviously, before the inventor's present work, these pore strips had not been used for the purpose of lifting and preserving bloody impressions. The component in the pore strip largely responsible for its ability to adhere to blood is titanium dioxide, which has effectively been used with methanol to develop bloody fingerprints on dark non-porous surfaces (Bergeron 2003). Each pore strip was cut into three, approximately 1"×1" pieces, due to the availability of only a limited size strip. The strips are not conducive for lifting any fingerprints larger than this at this time.

The lifting strip comes with a plastic liner that preserves the application side of the lifting strip, and it must be removed before applying the lifting strip to the bloody fingerprint. The lifting strip was applied directly on top of the bloody fingerprint with the shiny application side facing down. The lifting strip will be only slightly tacky when applied to the surface—just enough to prevent the lifting strip from sliding on the surface and possibly altering the bloody fingerprint. The lifting strip must then be activated using one of the reagents chosen in this study.

The reagents chosen in this study were tap water, 100% methanol, and Kodak Photo-Flo 200™ The inventor understands Photo-Flo 200™ to include Propylene glycol (57-55-6) (25-30%) and p-tert-octylphenoxy polyethoxyethyl alcohol (9002-93-1) (5-10%). These reagents were selected based on previous research, where each had been successfully used in activating titanium dioxide for the use in enhancing both latent and bloody fingerprints. (Bergeron 2003; Schiemer and others 2005; Williams and Elliott 2005). To activate the lifting strip, the analyst dipped an index finger in the reagent and then rubbed a minute amount of the reagent over the backside of the lifting strip. The porous backside of the lifting strip must be rubbed thoroughly to affix the bloody fingerprint to the lifting strip. In this study, ten trials were conducted using the above reagents for all seven of the chosen surfaces.

After activating the lifting strip using the above mentioned reagents, the lifting strip must dry completely before the bloody fingerprint can be lifted from the surface in which it had been deposited. Five prints from each of the activating reagents on all seven surfaces were cut in two diagonally. Half of the bloody fingerprints were air dried and half were dried with a blow dryer. The remaining five prints were also cut in two diagonally, but were only air dried.

After the lifting strip and surface were completely dried, the analyst removed the lifting strip from the surface. The best method found for removing the lifting strip was to start in one of the corners and to slowly peel the lifting strip from the surface in which the bloody fingerprint was deposited. The bloody fingerprint was then visibly present on the white background of the lifting strip, providing an inverted version of the bloody fingerprint. At the end of this process, the bloody fingerprint was permanently affixed to the lifting strip.

The analyst took the remaining five bloody fingerprints that were cut in two diagonally and treated one of the sides with ninhydrin using a spray method. Ninhydrin was chosen for this study because it is widely used in the forensic science community and is available in most crime laboratories. (Wallace-Kunkel and others 2004). It is primarily used as an enhancement reagent for latent fingerprints on porous surfaces creating deep purple colored ridge structure in the fingerprint. However, it has also been effective in enhancing bloody fingerprints on light colored surfaces due to its ability to affix to amino acids present in the blood. (Exline and others 2003; Sears and others 2005; Wallace-Kunkel and others 2004)

The overall results of this study were extraordinary on the non-porous and semi-porous surfaces tested. The Kodak Photo-Flo 200™ lifted all proteinaceous material from the non-porous and semi-porous surfaces providing excellent visualization of all the ridge structure present in the bloody fingerprint. The Kodak Photo-Flo 200™ provides the best results for activating the titanium dioxide lifting strip because it is a surfactant. The surfactant is important because it reduces the surface tension during the activation process. Therefore, it is applied smoothly over the backing of the lifting strip, preserving the porous backing, yet providing enough moisture to completely activate the lifting strip. (Schiemer and others 2005). As for the tap water used, it also lifted all proteinaceous material from the non-porous and semi-porous surfaces. Yet, it did not provide the same sharp defined ridge structure as that of the Kodak Photo-Flo 200™. The 100% methanol was also effective, but it did not provide enough moisture during the activation process to allow the lifting strip to completely affix with all the proteinaceous material in the bloody fingerprint. However, it did provide the same defined ridge structure as that of Kodak Photo-Flo 200™. In all trials, the majority of the bloody fingerprint was lifted from the non-porous and semi-porous surfaces using all three reagents, with the Kodak Photo-Flo 200™ providing the best results. (Table 1).

However, the porous surfaces provided less than satisfactory results. Due to the porosity of the surface material, the bloody fingerprints completely saturated the fabrics which provided difficulty during the lifting process. The lifting strips were only able to lift a faint outline of the bloody fingerprints from the porous surfaces with no visible ridge structure present. In all trials the bloody fingerprint remained on the porous surface after the lifting strip was removed.

TABLE 1

| Results of lift quality | | | |
|---|---|---|---|
| | Lift Quality | | |
| Surfaces | Water | Methanol | Kodak Photo-Flo |
| Nonporous Item #1 Black Plastic Garbage Bag | *** | ** | *** |
| Nonporous Item #2 Light Blue Plastic Folder | *** | ** | *** |
| Semiporous Item #3 Human Skin | *** | *** | *** |
| Semiporous Item #4 Black Leather Belt | *** | ** | *** |
| Semiporous Item #5 Brown Leather Belt | ** | ** | ** |
| Porous Item #6 Grey Polyester Fabric | * | * | * |
| Porous Item #7 Blue Denim Fabric | 0 | * | 0 |

0 = no proteinaceous material, no ridge structure
* = proteinaceous material, no ridge structure
** = proteinaceous material, ridge structure
*** = complete lift all proteinaceous material, ridge structure The drying times varied in this study, depending on the surface and the reagent that were used. The more porous the surface, the longer it took for the drying process, whether it was air dried or dried with a blow dryer. Also, the more porous the surface, there was an increased level of moisture needed in the lifting strip during the activation process. Increased amounts of moisture on the surface make it difficult to remove the lifting strip without tearing the backing of the strip. The reagent with the quickest drying time was methanol, followed by Kodak Photo-Flo 200™ and then water. Blow drying the items decreased the drying times drastically, but did not provide any further enhancement. (Table 2, 3). The blow drying times given in this experiment were not continuous; they were sporadic throughout the drying process due to time constraints of the analyst.

TABLE 2

| Average dry time for blow drying | | | |
|---|---|---|---|
| | Blow Dried: Average Drying Times (minutes) | | |
| Surface Porosity | Water | Methanol | Kodak Photo-Flo ™ |
| Non-porous | 8 | 5 | 10 |
| Semi-porous | 60 | 45 | 45 |
| Porous | 68 | 43 | 60 |

TABLE 3

| Average dry time for air drying | | | |
|---|---|---|---|
| | Air Dried: Average Drying Times (minutes) | | |
| Surface Porosity | Water | Methanol | Kodak Photo-Flo ™ |
| Non-porous | 40 | 15 | 35 |
| Semi-porous (human skin) | 10 | 10 | 10 |
| Semi-porous | 90 | 90 | 90 |
| Porous | 105 | 83 | 98 |

Furthermore, enhancement with ninhydrin was effective in producing greater ridge structure in the bloody fingerprints lifted from the various surfaces tested. However, the ninhydrin reacted with the components of the lifting strip, turning the strip a dark purple color and providing poor contrast for viewing the ridge structure that was previously available.

This study has shown that bloody fingerprints can be effectively lifted from non-porous and semi-porous surfaces using a lifting strip containing titanium dioxide. The reddish-brown ridge structure in the bloody fingerprints provides a nice contrast on the white background of the lifting strip which allows for excellent visualization of the ridge structure present. Therefore, subsequent enhancement after lifting the bloody fingerprints from the surface is not necessary. Also, when the lifting strip is activated, especially with Kodak Photo-Flo 200™, it enhances the quality of the bloody fingerprint, so an optimal quality bloody fingerprint is lifted. When utilizing this technique, bloody impressions can be removed from non-porous and semi-porous immobile objects at crime scenes and from human skin with ease. When the lifting strip is dried, the lifted print becomes permanently affixed to the surface preserving it for future use.

The results from this study will benefit the entire forensic science community. The ability to lift bloody impressions from various contrasting non-porous and semi-porous surface without the need for laboratory equipment or toxic chemicals is both convenient and can be done in a timely manner, especially with the use of a blow dryer to speed up the drying process.

As a result of this study and other investigation, the inventor determined a number of important points. First, the size of the strips needs to be altered to meet the needs of the forensic science community. The strips need to be big enough for lifting bloody fingerprints, bloody palm and foot impressions and bloody footwear impressions encountered at crime scenes. Basically, the strips should come in a variety of sizes including larger sizes.

Second, it is helpful to create a hinge lifting strip for bloody impressions similar to what is currently used for latent fingerprints. This allows the lift to be labeled, easily applied and activated; and it would help preserve the bloody impression for future analysis. Hinge lifting strips are well-known to persons of skill in the field of forensic science. They include an adhesive backed lifting film which comes with a lifting card. To use the hinge lifter, the lifting film is peeled from the lifting card, but a part of the film portion remains attached to the card on one end, thus forming a “hinge.” The lifting film is then applied to the surface to lift the latent print. The lifting film is pressed over the latent print and the print is lifted onto the film, which is then preserved with the backing card for future analysis. They also come with an area to label or diagram the location of the print. Hinge lifting strips for latent fingerprints are commercially available. Brand names include Sirchie® and BVDA®. But the hinge lifters for latent fingerprints need to be modified in accordance with the teachings of the invention, which involves lifting bloody impressions (e.g. using titanium dioxide).

Third, the backing on the commercially available Biore® lifting strip could be more durable. It degrades easily if too much moisture is added, destroying the lifting strip and impression during the lifting process. Therefore, one should alter the backing on the strip to create a more durable backing. Yet, a material should be selected to keep the backing material porous so the strip can still be easily activated without the possibility of altering or destroying the print.

Fourth, it is beneficial to increase the amount of titanium dioxide in the lifting strip to see if that would improve the quality of the bloody impressions lifted from various surfaces. The titanium dioxide is disposed in the impression layer of the lifting strip. The titanium dioxide comprises about 2 weight percent of that layer. The lifting qualities of the impression layer will increase with increases in the concentration of titanium dioxide.

An embodiment of the invention was used to lift bloody fingerprints off of seven surfaces. Two were nonporous: black plastic trash bags and a blue translucent folder. Three were semi-porous surfaces: human skin, black and brown leather. Two were porous items: grey polyester fabric and blue denim. There were 30 lifts from each sample. 10 lifts for each surface were activated with water, 10 were activated with methanol, and 10 were activated with Photo-Flo™—all of which activate titanium dioxide. Photo-Flo™ provided the best results. Five of the prints from each activation method were cut in half after activation. The top half was air dried and the bottom half was blown dry. The remaining five prints were also cut in half with the top half remaining as is and the bottom enhanced further with ninhydrin. The blow dryer is very effective in reducing the dry time before the lift can be removed.

Referring to the figures, one can see a preferred embodiment generally shown at 10. It includes a strip assembly for lifting and preserving bloody impressions including a lifting strip generally indicated at 12 having a backing layer 14, and an impression contact or impression bonding layer 16 carried by the backing layer, with the impression contact layer including titanium dioxide.

The pigment content in the impression contact layer 16 can range from 0.01 to 70% by weight based on the total weight of the ingredients in the impression contact layer 16. Possible pigments/extenders other than titanium dioxide (which has already been mentioned) include zinc oxide, silica, sericite, and kaolin.

The impression contact layer 16 typically includes enough titanium dioxide to bond with the bloody impression. In one embodiment, there is an amount ranging from about 2 weight percent and higher. The titanium dioxide is mixed with a variety of other ingredients as indicated in Example 8 disclosed in U.S. Pat. No. 6,306,382, the teachings of which are incorporated herein by reference. The ingredients can include, for example: polymethacryloyloxy trimethyl ammonium chloride (QDM) (MW: 200,000)—15.0 wt. %; polymethacrylamidepropyl trimethyl ammonium chloride (MAPTAC) (MW: 300,000)—15.0 wt. %; polyoxyethylene hydrogenated castor oil (E.O. 40)—1.5 wt. %; Squalene—0.5 wt. %; 2-ethylhexanoic triglyceride—2.0 wt. %; sorbitol—3.0 wt. %; kaolin—7.0 wt. %; titanium dioxide—2.0 wt. % and higher; ethanol—5.0 wt. %; antiseptic—suitable amount; and water—balance.

The polymer content of the impression contact layer 16 can affect the strength and durability of the contact layer. The amount of polymer in the impression contact layer 16 can range from 0.01 to 70% by weight based on the total weight of the ingredients in the impression contact layer 16. It may be desirable in some embodiments to have this polymer content range as high as 40% or higher to increase the strength and durability of the contact layer 16.

The assembly further includes a cover 18 for covering the impression contact layer 16. The cover 18 is some suitable clear plastic.

The assembly further includes a hinge 20 interconnecting the lifting strip and the cover. The hinge 20 may desirably include a strip where a legend or writing can be applied to describe or label the strip with a date, location, or other useful information.

Figure 3:
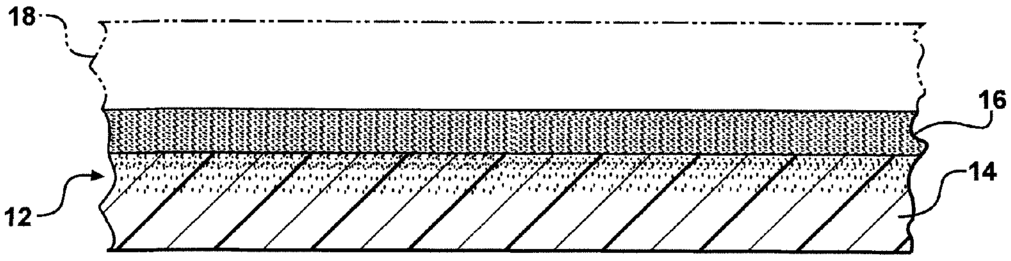
FIG. 3 is a side sectional view taken along lines 3-3 in FIG. 2 showing the layers of an embodiment of the strip.
Figure 4:
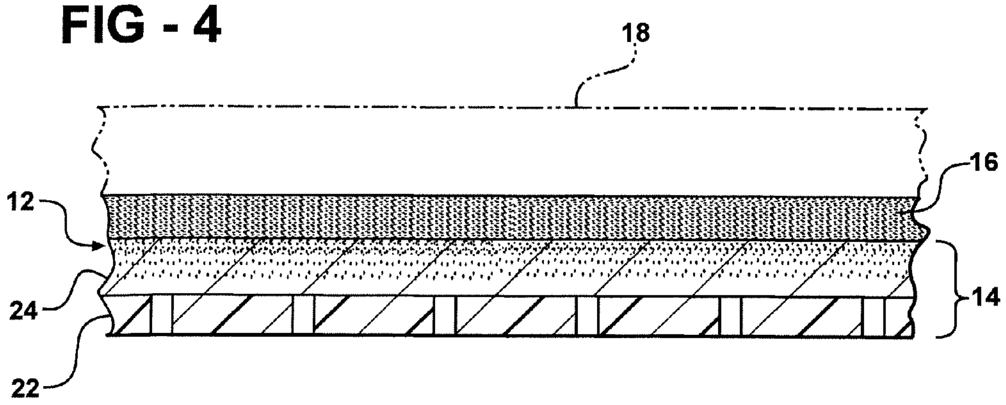
FIG. 4 is a similar side sectional view of an alternative embodiment.

In this embodiment, the backing layer 14 is light in color (e.g. white) to provide a contrasting background for the bloody impression to be lifted. The backing layer 14 includes hydrophobic material and hydrophilic material. In one embodiment, these materials may be combined into a single layer as shown in FIG. 3. In another embodiment, the hydrophobic material and hydrophilic material are in substantially separate layers 22 and 24, respectively, as shown in FIG. 4. Specific materials that can be used are set forth in U.S. Pat. Nos. 6,042,844 and 6,306,382, the teachings of which are incorporated herein by reference. Common hydrophobic materials are plastics and plastic fibers. Common hydrophilic materials are natural fibers like cotton, flax and wool.

The porosity of the backing layer 14 is, in one embodiment, less than 70%. The porosity is represented by the following equation:

$$\text{Porosity }(\%)=(\rho-\rho')\times 100/\rho$$

wherein $\rho$ is a specific gravity of the backing layer 14, and R' is an apparent specific gravity of the backing layer 14. The explanation for this embodiment is that there is a tradeoff between permeability and strength. Backing layers that are more porous tend to be more permeable, but not as strong. In some embodiments, it may be desirable to have a stronger backing layer. This may increase the drying time, but that could be a worthwhile tradeoff.

The thickness of the backing layer 14 can range from 40 to 2000 μm. This can be divided fairly evenly between the two sub-layers 22, 24 if there are any. In some embodiments it could be desirable to increase the thickness above 2000 μm to increase the strength of the backing layer.

The use of the strip assembly 10 is illustrated in part in FIG. 1. An investigator can first obtain a strip assembly 10 and peels back the cover 18. Next, the investigator applies the strip to a bloody impression (e.g. a fingerprint). Then the investigator applies a surfactant like Photo-Flo 200™ to the backing layer 14 to interact with the materials in the impression contact layer 16. Then the investigator dries the strip, either with air drying or with a blow dryer. Finally, after drying, the investigator can lift the strip carefully and replace the cover 18 to protect the impression. The impression can be labeled and taken to a lab for analysis, and possibly used as evidence.

Disclosed now are other, newer embodiments of the invention as discussed below. According to one, there is an improved backing or support layer 14, and an improved bonding layer 16. In general, the support layer comprises a porous, water-permeable polymer membrane which is coated on one or both sides with fine particles of titanium dioxide. The titanium dioxide coating may include other helpful constituents. When the strip is to be used, a titanium dioxide coated side is wetted with methanol or the like and applied to a bloody impression. After a brief drying period, the impression is ready for lifting and preserving.

The backing layer 14 includes a suitable porous and water permeable polymer membrane. Suitable membranes include nylon transfer membranes for nucleic acids like: Pall Life Sciences Biodyne B Membrane (with pore size of 0.45 μm); Pall Life Sciences Biodyne A Membrane (with pore size of 0.45 μm); Pall Life Sciences Biodyne Plus Membrane (with pore size of 0.45 μm); and Pall Life Sciences BioTrace NT Membrane. Other suitable membranes include PVDF membranes like Pall Life Sciences BioTrace PVDF Membrane; and Millipore Immobilon-P PVDF Membrane (with pore size of 0.45 μm). Still other membranes include Schleicher & Schuell Nytran Membrane (with pore size of 0.2 μm); Whatman Nytran N Membrane (with pore size of 0.2 μm); Whatman Nytran SPC Membrane; Whatman PVDF Membrane; BioRad nitrocellulose; BioRad PVDF; and Sigma Aldrich BioBond nylon Membrane. These transfer membranes feature binding capacities to allow the retention and transfer of protein and related material for study and preservation. This is useful in lifting bloody impressions.

Of these backing layers, the Pall Life Sciences Biodyne B Membrane (0.45 μm) is preferred. According to its material data sheet, it is made from nylon 6,6 on an integral non-woven polyester support. The pore surfaces are cationic and contain a high density of quaternary ammonium groups. The membrane resists heat and solvents.

The improved bonding layer 16 is formed using a dispersion of titanium dioxide particles in a suitable water miscible vehicle or dispersant. The liquid dispersion may also include other ingredients for enhancing the lifting of a bloody impression. Such additional materials include an acid, a surfactant/emulsifier, and a polymer.

Suitable titanium dioxides include KalOpaque 820 Treated Rutile Titanium Dioxide (0-10% Aluminum hydroxide); J. T Baker 'Baker Analyzed' Titanium Dioxide (0-1% water soluble salts, Arsenic, Iron, Lead, and Zinc); KalOpaque CA Anatase Titanium Dioxide; Kerr-McGee CR-837 Rutile Titanium Dioxide; Kerr-McGee 100 Anatase Titanium Dioxide; Ken-McGee CR-880 Titanium Dioxide.

Suitable acids include 5-Sulfosalicylic acid dihydrate, and acetic acid. At least the 5-Sulfosalicylic acid dihydrate acts as a fixative for blood. In this way, it cooperates with the other ingredients in lifting and preserving the bloody impression. This is important because it will help preserve the integrity of the bloody impression when the lifting strip is applied to the surface by fixing it to the lifting strip and not dispersing the blood on the surface destroying the impression in the process.

Suitable surfactants/emulsifiers include Liqui-Nox Detergent: Sodium Dodecylbenzenesulfonate; and Kodak Photo-Flo 200: Propylene glycol and p-tert-octylphenoxy polyethoxyethyl alcohol. The surfactants/emulsifiers help disperse the titanium dioxide onto and into the backing layer 14.

Suitable polymers include Polyvinyl alcohol; Polyvinyl chloride; Polyvinyl fluoride; Nylon 6,6; Polyvinylidene fluoride; Polyacrylic acid; Polyquaternium 37; Polysilicone-13; Polyethylene; Polypropylene; and Polyether Sulfone. Polyvinyl alcohol is the preferred polymer at this point because it is water soluble and has excellent film forming, emulsifying and adhesive properties. Polymers are useful in this formula because they help suspend the mixture on the backing layer 14 and improve the overall adhesive properties of the lifting strip.

Suitable liquid vehicles for forming the dispersion include water, butylene glycol, and propylene glycol.

Other ingredients could be used in the mixture, including various preservatives (e.g. methyl paraben, ethyl paraben, propyl paraben, and butyl paraben).

One suitable bonding layer mixture includes 0.13 grams KalOpaque 820 Treated Rutile Titanium Dioxide (0-10% Aluminum hydroxide); 2 grams 5-sulfosalicylic acid dihydrate; 33 ml Kodak Photo-Flo 200: Propylene glycol and p-tert-octylphenoxy polyethoxyethyl alcohol; 10 ml polyvinyl alcohol; and 33 ml water. Another suitable mixture includes 0.2 grams KalOpaque 820 Treated Rutile Titanium Dioxide (0-10% Aluminum hydroxide); 1 gram 5-sulfosalicylic acid dihydrate; 25 ml Kodak Photo-Flo 200: Propylene glycol and p-tert-octylphenoxy polyethoxyethyl alcohol; 25 ml polyvinyl alcohol; and 50 ml water. Larger or smaller batches with similar proportions should also work well. Another effective bonding layer mixture includes 0.13 grams KalOpaque 820 Treated Rutile Titanium Dioxide (0-10% Aluminum hydroxide); 1.7 grams 5-sulfosalicylic acid dihydrate; 33.3 ml Kodak Photo-Flo 200: Propylene glycol and p-tert-octylphenoxy polyethoxyethyl alcohol; 16.7 ml polyvinyl alcohol; and 33.3 ml water. The KalOpaque 820 is available from Kalamazoo Paper Chemicals, a division of Joyceco Corp., 8782 Gull Road, Richland, Mich. 49083.

Thus, in more general terms, one can create the formula by starting with a dry unit of titanium dioxide and also using 5-14 dry units of 5-sulfosalicylic acid dehydrate. Separately one can start with a liquid unit of Kodak Photo-Flo 200 (Propylene glycol and p-tert-octylphenoxy polyethoxyethyl alcohol) and mix it with ½ to 1 liquid unit of polyvinyl alcohol and a quantity of water that can range from 1-2 parts. The dry and liquid units can be mixed together in any order.

The embodiments can be made by mixing the bonding layer ingredients in a mixing vessel. The titanium dioxide should be thoroughly mixed and dispersed in the liquid suspension in small particle form, with attention to avoid clumping. A whisk or the like can be used to disperse the titanium dioxide in the liquid suspension. Then the next step is saturating the backing layer membrane 14 with the mixture of bonding layer ingredients. This can be accomplished, for example, by dipping the backing layer membrane 14 in the bonding layer mixture, and then making some effort to coat onto, and even embed or impregnate the titanium dioxide into, the membrane. The membrane can be handled with nitrile or non-latex gloves. Latex gloves contain traces of protein, which may leave proteinaceous residue behind due to the lifting strips' high affinity for proteins.

One technique is to use a shallow tray for coating the membrane, and push the membrane to the bottom of the tray and rub it into the particles that fall to the bottom of the tray. It is desirable in this procedure to bond the particles to the membrane in their smallest particle form. After the membrane is well-coated with the mixture, including the titanium dioxide particles, the next step is removing it and allowing it or causing it to dry, e.g. by air drying. When completely dried, the lifting strips are sealed in plastic bags and stored for future use. The bonding layer mixture provides a white surface, which affords excellent contrast with the bloody impressions that are to be lifted.

FIG. 3 shows a version of this embodiment. The bonding layer mixture can be coated on the backing layer membrane to form a layer 16 on top of the backing layer membrane 14. Some of the bonding layer mixture will penetrate into or impregnate the backing layer membrane 14, which is porous. If the backing layer membrane 14 is submerged or otherwise fully coated with the bonding layer mixture, there would be a layer on both the top and bottom sides of the backing layer membrane 14 with the mixture penetrating the layer from both sides. The inventor noticed that, at least with the Pall Life Sciences Biodyne B Membrane, there is a preferred bonding side to the membrane. The dull or inner most facing side of the membrane roll is observed to have an increased binding capacity and is the preferred lifting side, so at least this side should be coated with the bonding layer mixture.

Furthermore, the lifting strips composed in this manner have an inherent fluorescent/fluorogenic property when fluorophores are lifted onto the membrane and excited by the use of an Alternate Light Source (ALS) or Laser. The intrinsic fluorophores found in proteins and amino acids, such as tryptophan, tyrosine, and phenylalanine are naturally fluorescent. When these intrinsic fluorophores found in bloody and other impressions are lifted and immobilized on the lifting strip within close proximity of the formulation dispersed onto the lifting strip with the titanium dioxide and silver hydroxide in small particle form, Metal Enhanced Fluorescence (MEF) is believed to be achieved. Other metals that would be suitable for MEF include, but are not limited to aluminum, nickel, silver, iron, platinum, palladium, and gold. The fluorescence achieved as a result of this phenomenon has been reported to increase fluorescence by several million-fold (Chowdhury and others 2009; Geddes and Lakowicz 2002; Ray and others 2007; Szmacinski and others 2008).

At this point, the highly fluorogenic strips are sensitive to bonding with proteins, so care should be taken to avoid touching the strips to any proteins other than the proteins that are the subject of lifting at the crime scene or elsewhere. This includes the use of latex gloves when handling or using the lifting strip, because an ALS or laser can reveal protein residues left by latex gloves.

There is also an improved method of using the new embodiments. The method includes the steps of saturating the embodiment with an alcohol, preferably methanol but suitably ethanol, and then applying the saturated sheet to the bloody fingerprint. The lifting strips are removed from the plastic bags in which they are stored and are activated with an alcohol based reagent, either 50% methanol or 50% ethanol. The alcohol enhances wetting of non-wetting surfaces like the protein membranes. The alcohol can also assist in lifting the protein material in the bloody impression. Furthermore, methanol is also a fixative for blood. The activating alcohol is applied directly to the titanium dioxide bonded side or the dull side of the lifting strip using a plastic pipette or spray bottle until the lifting strip is completely saturated. Upon saturation, the lifting strip should be air dried for less than a minute to prevent any pooling of the alcohol on the lifting strip. When ready to use, the lifting strip will be completely moist without any observable wet areas. Pooling of the activating alcohol on the lifting strip could obviously alter the bloody impression during the application of the lifting strip and care should be taken to avoid this from occurring. Once activated with the alcohol and slightly dried, the lifting strip is placed directly on top of the bloody impression with the titanium dioxide or dull side down. Adequate pressure should than be applied to the backside of the lifting strip to completely affix the bloody impression to the lifting strip. When lifting smaller or non-porous impression, the amount of pressure applied by the hand is adequate. If lifting larger or porous impressions an ink roller can be used to increase the amount of pressure over the area in a shorter time. Within 1-2 minutes the lifting strip is dried and can easily be removed from the surface lifting the bloody impression onto the contrasting white background of the lifting strip for analysis.

The inventor discovered that, after the lifting strip is dried, the lifting strip is further unique because of its added benefit of inherent fluorescence when visualized with an ALS or Laser. Lifted bloody impressions can be excited by these light sources to fluoresce bloody and other impressions to a bright orange color at a setting optimized at 505 nm using orange goggles, further providing an improved contrast for visualization. The resulting fluorescence is highly sensitive for proteins, fluorescing impressions and bloody impressions that could not be visualized under normal lighting conditions.

Leucocrystal Violet (LCV) is a protein dye that has been used successfully as a subsequent enhancement technique for bloody impressions that were lifted with the lifting strip. The lifted reddish-brown bloody impressions turned a dark purple color under normal lighting conditions when treated with LCV. Yet, after the treatment with LCV the background of the lifting strip was turned a light purple color, which decreased the contrast that was previously visible. The lifted impressions could also be visualized after using LCV with an ALS. The ALS created a bright orange fluorescence when visualized with orange goggles optimized at 530 nm, which improved the contrast for analysis. However, since the discovery of the inherent fluorescent properties of the lifting strip it was apparent that the LCV was quenching (i.e., diminishing) the inherent fluorescence provided by the lifting strip. Therefore, subsequent enhancement for the purpose of fluorescence is not necessary or recommended with the use of this product.

These new embodiments represent an improvement over the older embodiments. In the older embodiments, the lifting strips were purchased pre-made from manufacturers, such as the lifting strip by Kao Brands and the Meijer lifting strip by Haba-Davion. These lifting strips were then activated with a variety of reagents to make an effective lifting strip for lifting bloody impressions. The previously used lifting strips were only available in limited sizes and were manufactured for cosmetic use and not for the needs of forensic science. Accordingly, these strips have several drawbacks. First, the backing layer on these lifting strips tended to crack and otherwise degrade over time. Second, these lifting strips did not necessarily include titanium dioxide; and if they did, the titanium dioxide was not concentrated enough, of a high enough grade or quality, or uniformly distributed enough for lifting bloody impressions. Also, these lifting strips did not include other additives and features that enhance the lifting and preserving of bloody impressions. Finally, the backing layer on the commercially available strips had material that took a long time to dry even with a blow dryer. Due to the limitations of the available lifting strips, an improved lifting strip was developed and manufactured by the inventor in the laboratory to better suit the needs of the forensic science community. Furthermore, the inherent fluorescence of the lifting strips, when visualized with an ALS or laser, provides a highly sensitive fluorescent impression or bloody impression with an optimal contrast for analysis.

Obviously, many modifications and variations of the present invention are possible in light of the above teachings. Therefore, it is to be understood that within the scope of the appended claims the invention may be practiced otherwise than as specifically described. Moreover, the reference numerals are merely for convenience and are not intended to be in any way limiting.

The invention claimed is:

1. A method of lifting bloody impressions from a surface including the steps of:

providing a backing sheet having titanium dioxide disposed thereon;

applying a liquid to the sheet to wet the titanium dioxide;

applying the wetted sheet to a bloody impression; and lifting the backing sheet to remove at least an identifiable portion of the impression from the surface.

2. The method of claim 1 wherein the liquid includes water-miscible alcohol.

3. The method of claim 2 wherein the alcohol is applied to the side of the sheet that is to be applied to the impression.

4. The method of claim 2 further including the step of eliminating any pooling of the alcohol before applying the wetted sheet to the impression.

5. A strip material for pressing against a bloody impression on a surface and precisely lifting the bloody impression from the surface and preserving it on the material, the strip material comprising:

a porous polymer membrane strip having a coating layer on at least one side of the membrane, the membrane being permeable to water and water miscible alcohols, the coating comprising particles of titanium dioxide in a size and amount for wetting with water or a water miscible alcohol, wherein the coating further comprises an organic acid for fixing blood from the impression to the coating.

6. The strip material of claim 5 where in the coating layer comprises a polymeric binder for fixing the titanium dioxide particles to the membrane strip.

7. The strip material of claim 5 in which the acid comprises 5-sulfosalicylic acid or its dihydrate.

8. The strip material of claim 5 wherein the coating layer includes a surfactant.

9. The strip material of claim 8 wherein the surfactant includes propylene glycol and p-tert-octylphenoxy polyethoxyethyl alcohol.

10. The strip material of claim 5 wherein the coating layer includes a polymer.

11. The strip material of claim 10 wherein the polymer includes polyvinyl alcohol.

12. The strip material of claim 5 wherein the membrane strip has a predetermined size large enough to lift a variety of bloody impressions.

13. The strip material of claim 5 wherein the polymeric membrane includes a polymer transfer membrane having pores.

14. The strip material of claim 13 wherein the polymer transfer membrane includes nylon.

15. A lifting strip assembly for lifting and preserving bloody impressions found on a variety of surfaces including:

a lifting strip including a support layer and an impression bonding layer carried on the support layer, the bonding layer having a material including titanium dioxide adapted to bond with the material in a bloody impression, and to lift and preserve at least a portion of the impression intact; and a transparent protective layer hingedly attached to the lifting strip whereby the protective layer can be disposed over the bonding layer to cover and protect the impression after it has been lifted.

16. The lifting strip of claim 15 wherein the bonding layer includes at least one of the following: an acid, a surfactant, and a polymer.

17. A method of making a lifting sheet for lifting bloody impressions including the steps of:

obtaining a porous polymeric backing sheet;

preparing a coating material including titanium dioxide and at least one of the following: an acid, a surfactant, and a polymer;

dispersing the titanium dioxide uniformly throughout the coating material;

coating at least one side of the backing sheet with the coating material; and drying the coating material to fix it on the backing sheet.

18. A strip material for pressing against an impression on a surface and precisely lifting the impression from the surface and preserving it on the material, the strip material comprising:

a porous polymer membrane strip having a coating layer on at least one side of the membrane, the membrane being permeable to water and water miscible alcohols, the coating comprising an organic acid and particles of titanium dioxide in a size and amount for wetting with water or a water miscible alcohol and then being pressed against the impression to transfer and receive the impression onto the coating and, after drying of the wetting liquid, lifting from the surface.

19. A method of lifting impressions from a surface, where the lifted impression has fluorescent properties when viewed with a predetermined type of lighting, the method including the steps of:

providing a backing sheet having titanium dioxide and at least one other metal oxide disposed thereon;

applying a liquid to the sheet to wet the titanium dioxide and the at least one other metal oxide;

applying the wetted sheet to an impression; and lifting the backing sheet to remove at least an identifiable portion of the impression from the surface.

* * * * *